(12) United States Patent
Mische

(10) Patent No.: US 8,007,498 B2
(45) Date of Patent: Aug. 30, 2011

(54) METHODS AND DEVICES FOR TREATMENT OF BONE FRACTURES

(76) Inventor: Hans A. Mische, St. Cloud, MN (US)

( * ) Notice: Subject to any disclaimer, the term of this patent is extended or adjusted under 35 U.S.C. 154(b) by 109 days.

(21) Appl. No.: 09/733,775

(22) Filed: Dec. 8, 2000

(65) Prior Publication Data

US 2002/0032444 A1    Mar. 14, 2002

Related U.S. Application Data

(60) Provisional application No. 60/169,778, filed on Dec. 9, 1999, provisional application No. 60/181,651, filed on Feb. 10, 2000, provisional application No. 60/191,664, filed on Mar. 23, 2000.

(51) Int. Cl.
 *A61B 17/56* (2006.01)
 *A61B 17/70* (2006.01)
 *A61B 17/58* (2006.01)
 *A61F 2/06* (2006.01)
 *A61F 2/44* (2006.01)

(52) U.S. Cl. ........ 606/63; 606/60; 606/61; 606/62; 606/67; 606/68; 606/70; 606/95; 606/96; 606/93; 606/97; 606/98; 606/99; 606/100; 606/101; 606/102; 606/103; 606/104; 623/1.2; 623/1.23; 623/1.12; 623/1.11; 623/17.11; 623/17.12; 623/17.13; 623/17.14; 623/17.15; 623/17.16

(58) Field of Classification Search ............. 606/60–63, 606/67, 68, 70, 72, 86, 93, 95–104, 108; 623/1.2, 1.23, 1.11, 1.12, 17.11–17.16
See application file for complete search history.

(56) References Cited

U.S. PATENT DOCUMENTS

| | | | | | |
|---|---|---|---|---|---|
| 3,710,789 | A | * | 1/1973 | Ersek | 606/60 |
| 4,627,434 | A | * | 12/1986 | Murray | 606/63 |
| 4,969,888 | A | * | 11/1990 | Scholten et al. | 606/94 |
| 6,127,597 | A | * | 10/2000 | Beyar et al. | 606/86 |
| 6,248,110 | B1 | * | 6/2001 | Reiley et al. | 606/93 |

FOREIGN PATENT DOCUMENTS

| EP | EP 0 819 413 | * | 1/1998 |
|---|---|---|---|
| EP | EP 0 819 413 A2 | * | 1/1998 |

* cited by examiner

*Primary Examiner* — Patricia Bianco
*Assistant Examiner* — Nihir Patel
(74) *Attorney, Agent, or Firm* — Kinney & Lange, P.A.

(57) ABSTRACT

A method and devices for facilitating fixating and joining of bone fractures utilizing expandable devices that are positioned within the bone and across the fracture site. The stress from the expanded may enhance and expedite bone healing.

7 Claims, 13 Drawing Sheets

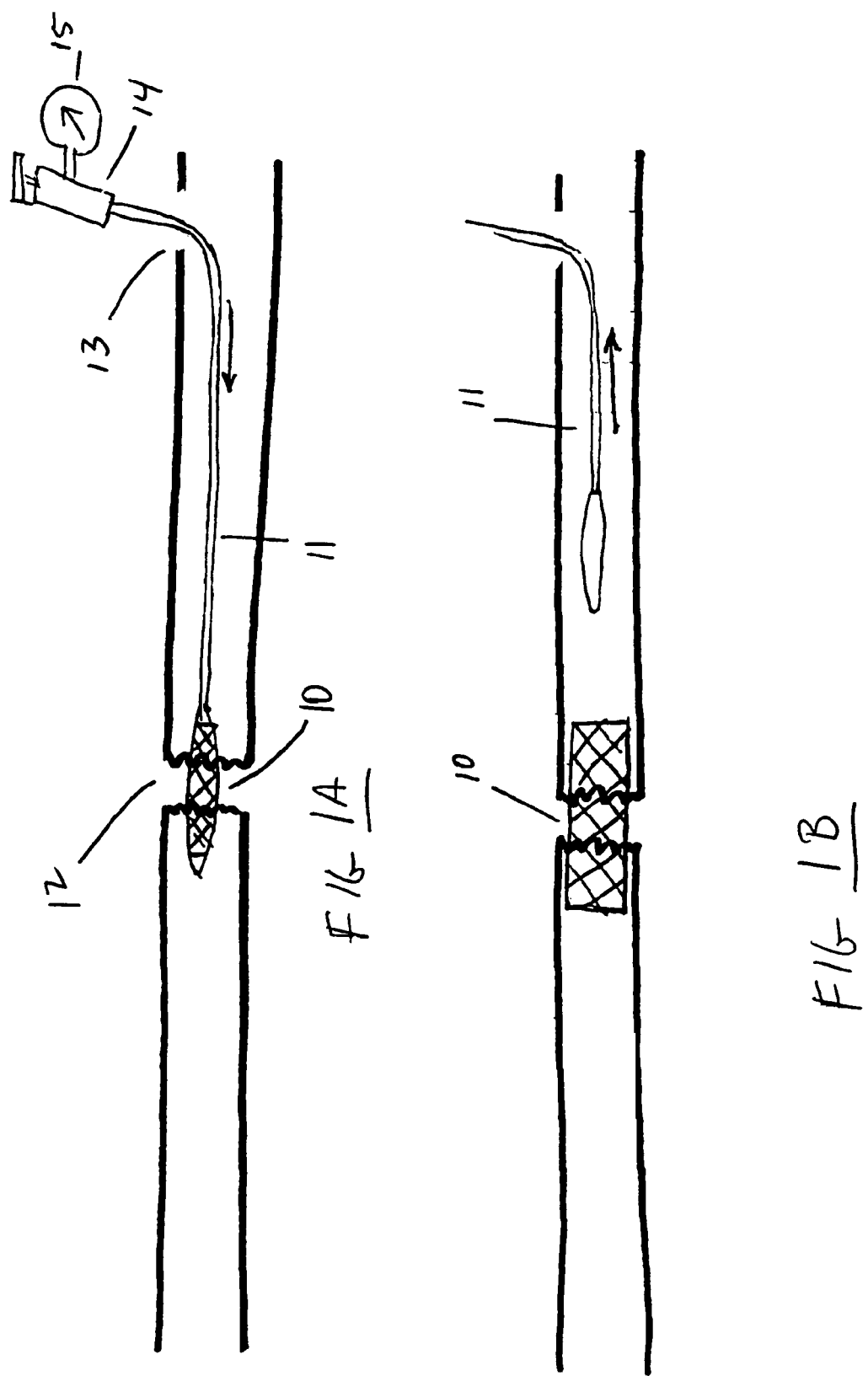

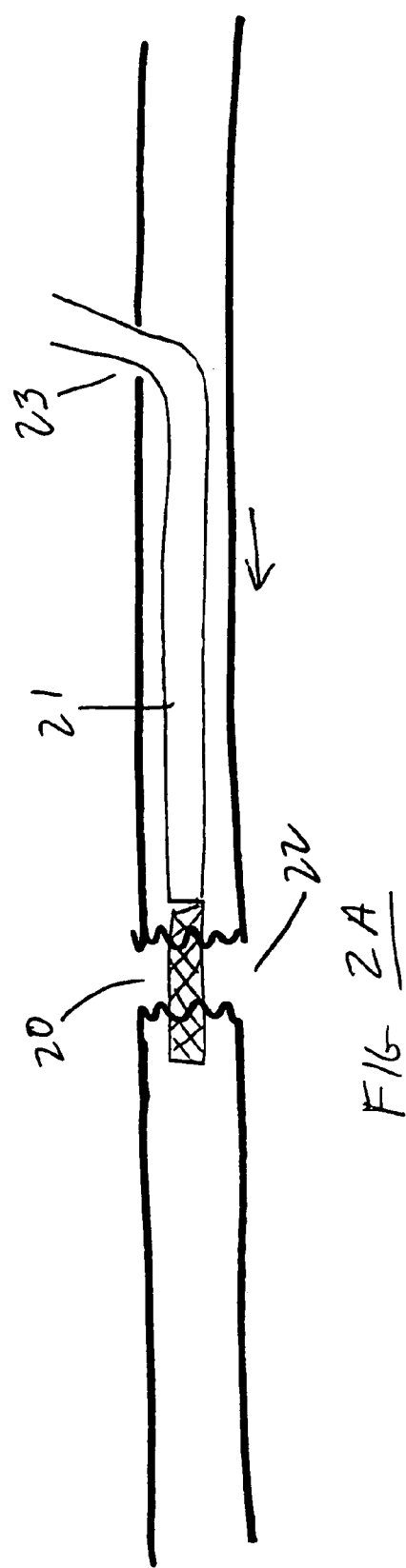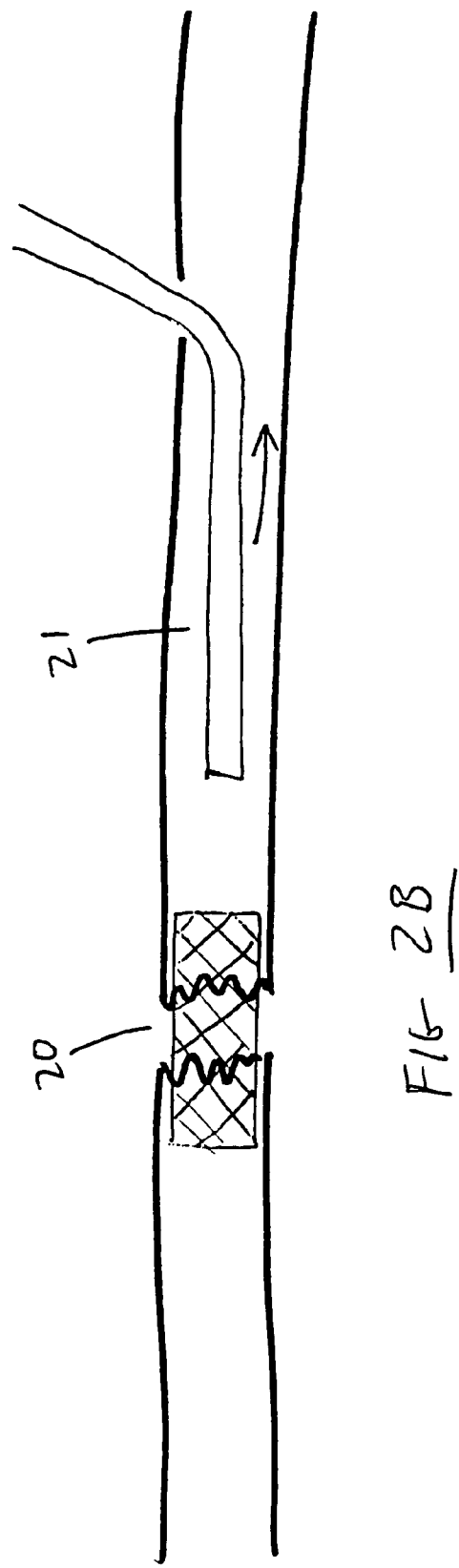

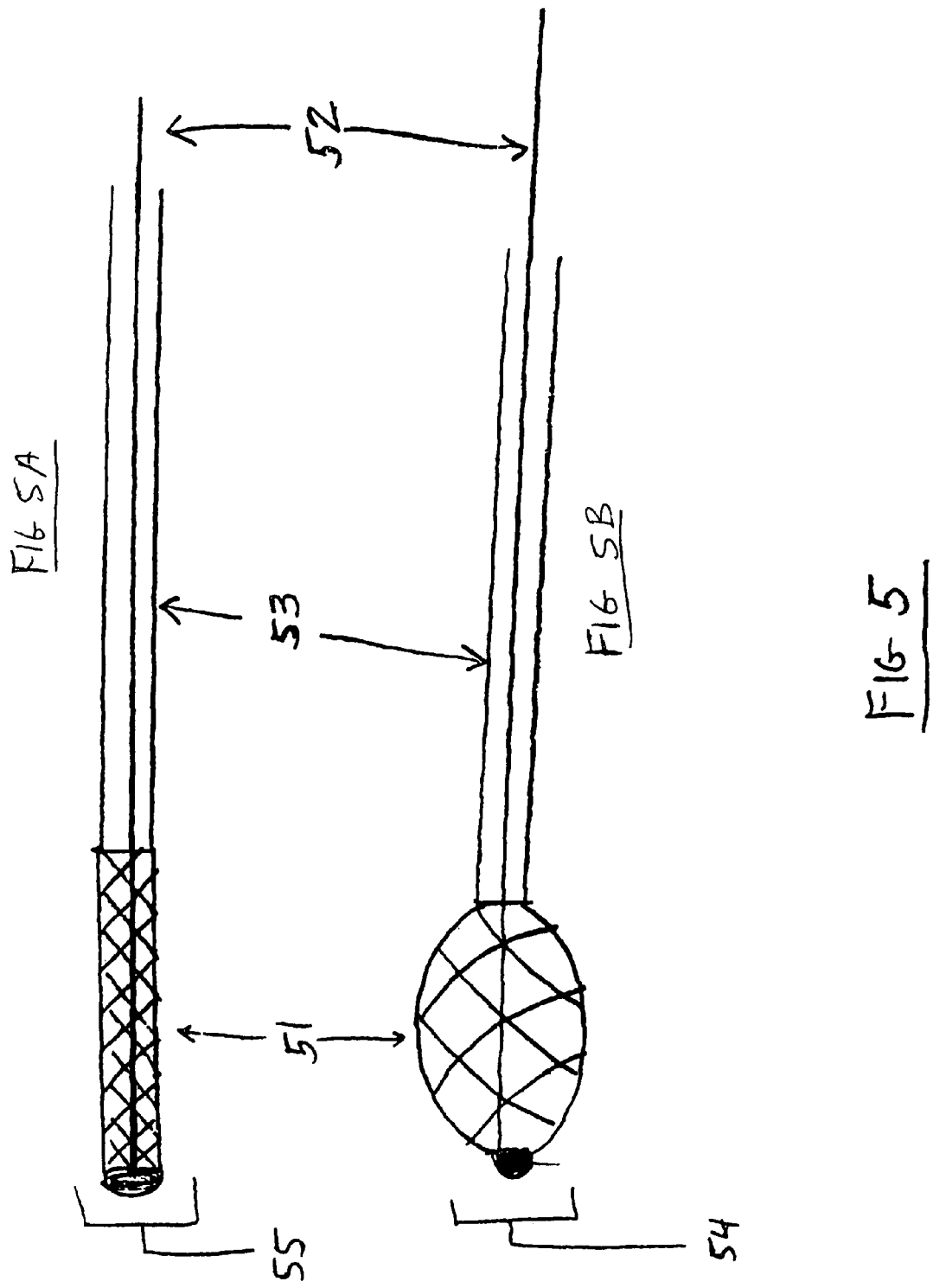

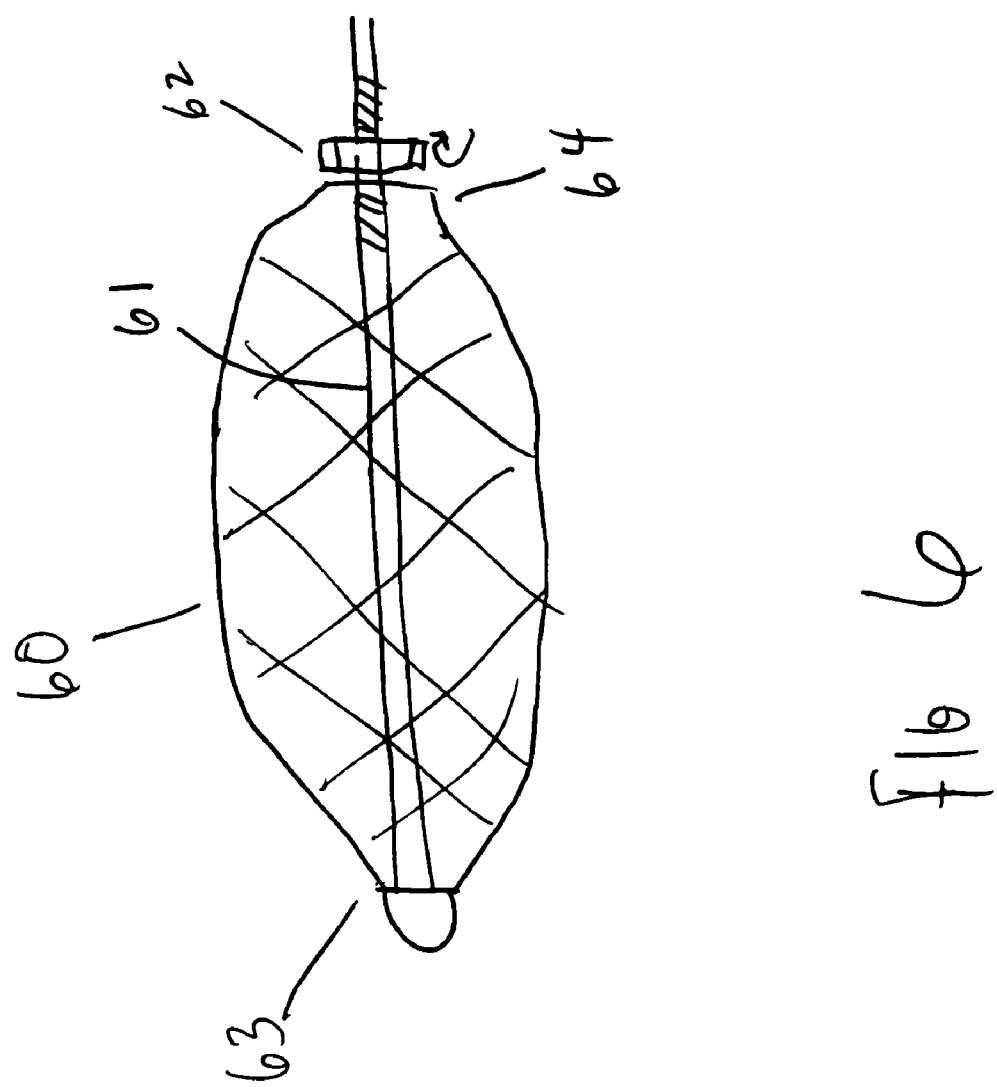

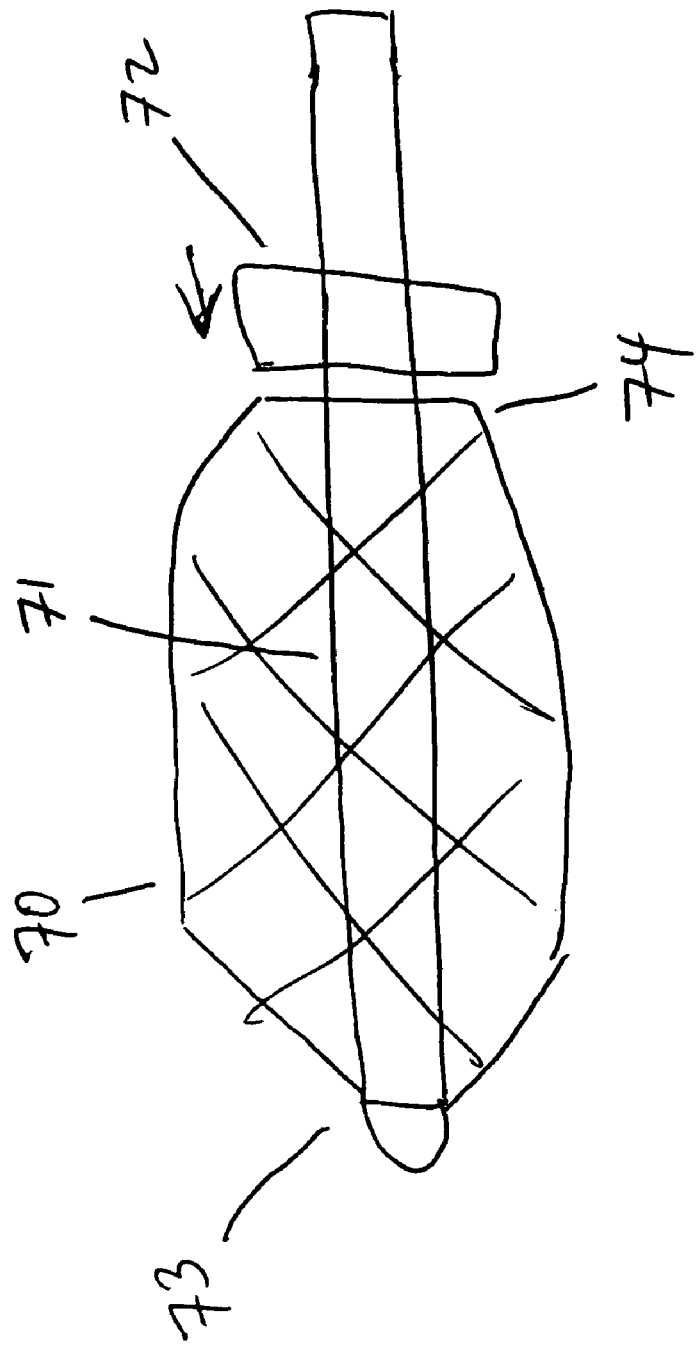

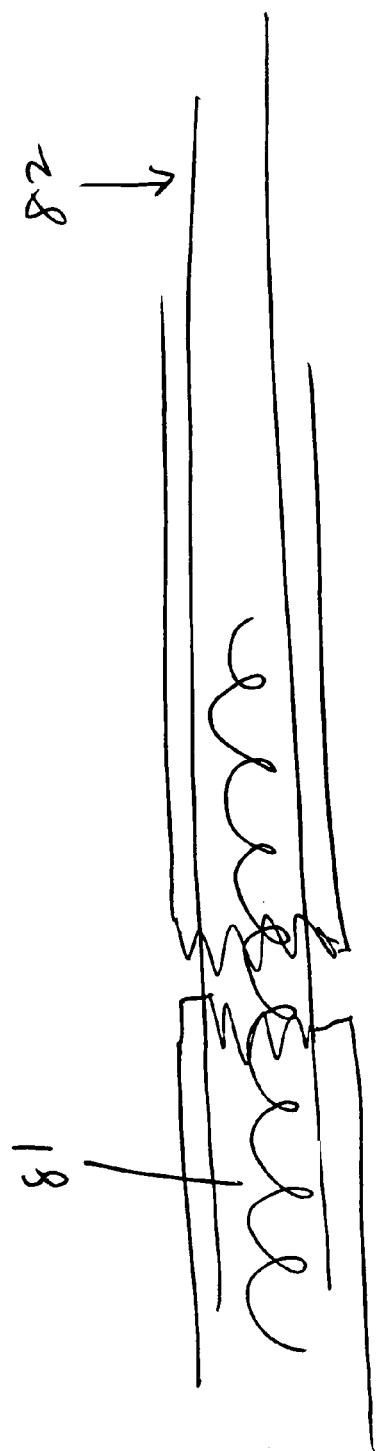
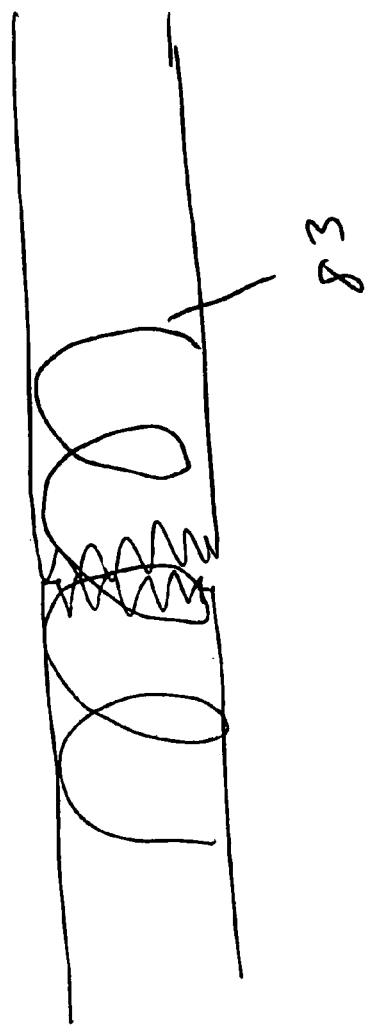

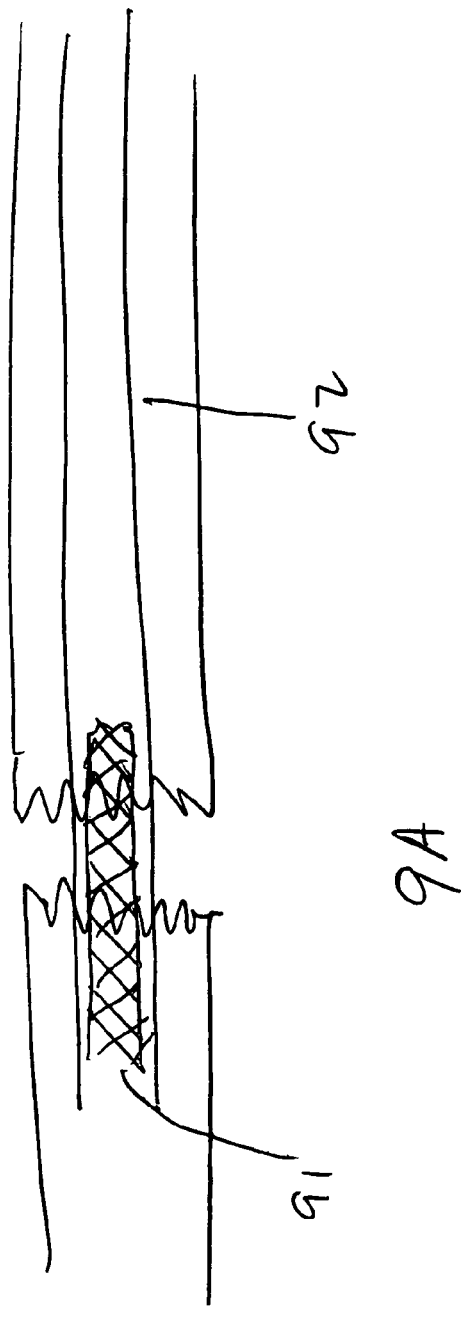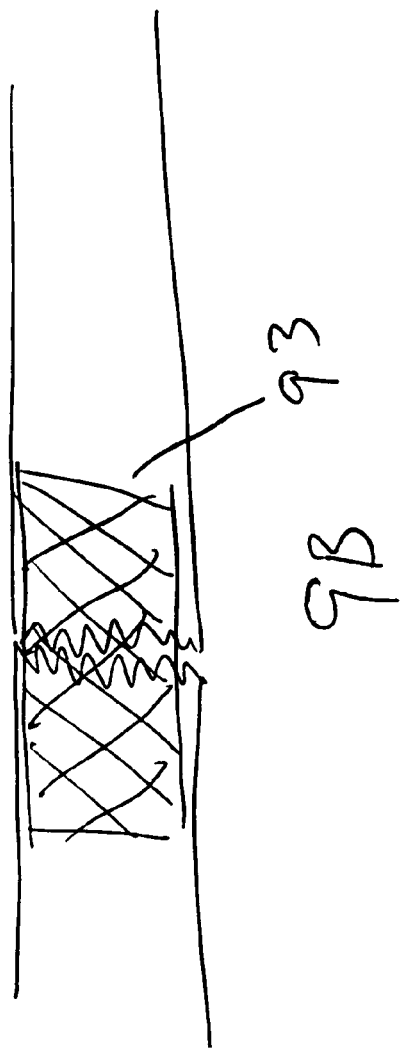

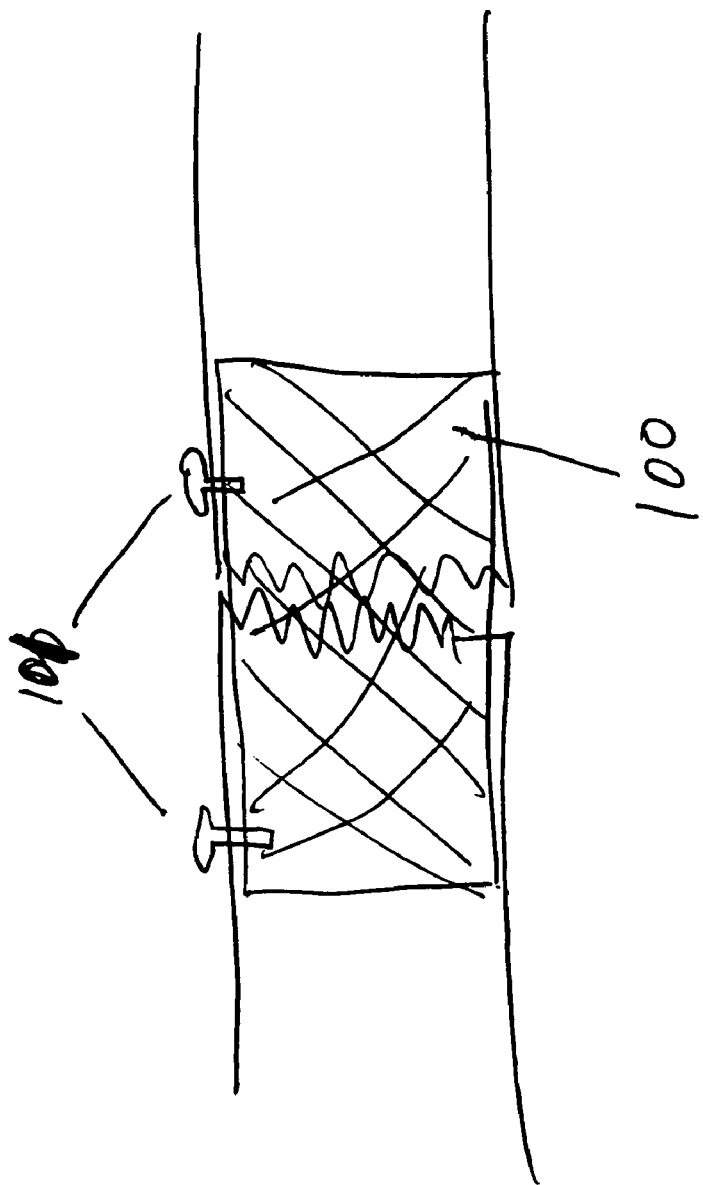

METHODS AND DEVICES FOR TREATMENT OF BONE FRACTURES

CROSS-REFERENCE TO RELATED APPLICATIONS

I claim the benefit of provisional applications with Ser. No. 60/169,778 filed Dec. 9, 1999, 60/181,651 filed Feb. 10, 2000 and 60/191,664 filed Mar. 23, 2000.

FIELD OF THE INVENTION

The present invention relates generally to the treatment of bone fractures utilizing expandable fracture fixating devices within the medullary cavity of bones, and equipment and methods specially designed for implanting these devices.

BACKGROUND OF THE INVENTION

The current methods of treating bone fractures ranges from simple setting of the bone and constraining motion via a cast or wrap to using pins, screws, rods and cement to fixate fracture site. With the use of casts, the bone is not stabilized and misalignment may occur after placing the cast. This may require the cast to be removed and the bone reset. This is a very uncomfortable and painful procedure for the victim and can ultimately result in permanent misalignment of the healed bone. The treatment modalities requiring a surgical procedure are painful and are associated with a high rate of complications. Post-procedural infections are one of the major complications associated with these surgical procedures. Many of these infections result in necrosis of bone and tissue and require additional surgical interventions and therapy. The invention discussed here provides for a unique and novel means of treating a variety of bone fractures with minimally invasive techniques and low complication rates.

SUMMARY OF THE INVENTION

In contrast to the prior art, the present invention proposes treatment of bone fractures using minimally invasive techniques, methods, equipment and devices to position and deliver an expandable fracture fixating device into the medullary cavity (marrow conduit). The device is preferably an expandable structure that "bridges" the fracture site and fixates the site upon expansion. In addition to fixation, the device also joins the fractured bone such as in the case of a compound fracture. Referring to the device as a bridge, the BRIDGE is substantially hollow and has low surface area and mass, the majority of bone marrow volume can be preserved. The ability to preserve a large quantity of the bone marrow cavity is beneficial for healing, bone health and maintaining the body's natural ability to generate red blood cells. In addition, the stress applied to the bone by the expanded or expanding "BRIDGE" facilitates rapid bone growth and strength. The operable level of stress applied to the bone will vary from low levels to high levels dependent on the type, size and location of bone to be treated. It is also envisioned that the BRIDGE can be used to expand and support bones that are crushed or compressed. The BRIDGE can be delivered by a variety of expansion devices, can be self expanding to due to inherent spring forces within the BRIDGE structure, or can be expansively actuated utilizing elements and mechanisms within the BRIDGE structure. These various devices and alternative embodiments will be detailed further.

Although standard medical equipment may be used to facilitate the procedure, it may be necessary to design unique, specialized tools in order for this invention to be properly utilized. These devices may include tissue separators, retractors, drills, introducers, coring tools, and others.

The invention is disclosed in the context of treating bone fractures but other organs and anatomical tissues are contemplated as well. For example, the invention may be used to treat spinal stenosis, individual vertebrae, and support or fixate segments of the spinal column. Likewise, a broken nose, sinus cavity or collapsed lung can be supported using this invention. Pelvic fractures in females could also benefit from placing this device within the vaginal cavity in order to support and fixate the pelvis or pubic bone.

BRIEF DESCRIPTION OF THE DRAWINGS

Throughout the several views of the drawings several illustrative embodiments of the invention are disclosed. It should be understood that various modifications of the embodiments might be made without departing from the scope of the invention. Throughout the views identical reference numerals depict equivalent structure wherein:

FIG. 1 is a diagram showing the advancement and deployment of the BRIDGE utilizing a catheter with an expandable element FIG. 2 is a diagram showing the advancement and deployment of a self-expanding BRIDGE FIG. 6 shows a bridge that can be expanded or contracted by relative movement of the ends of the structure FIG. 7 shows a bridge that can be expanded or contracted by relative movement of the ends of the structure FIGS. 8A & 8B show the placement of a coil BRIDGE FIGS. 9A & 9B show the placement of a braided BRIDGE FIG. 10 shows the screws or nails used in conjunction with an implanted BRIDGE

Figure 3A:
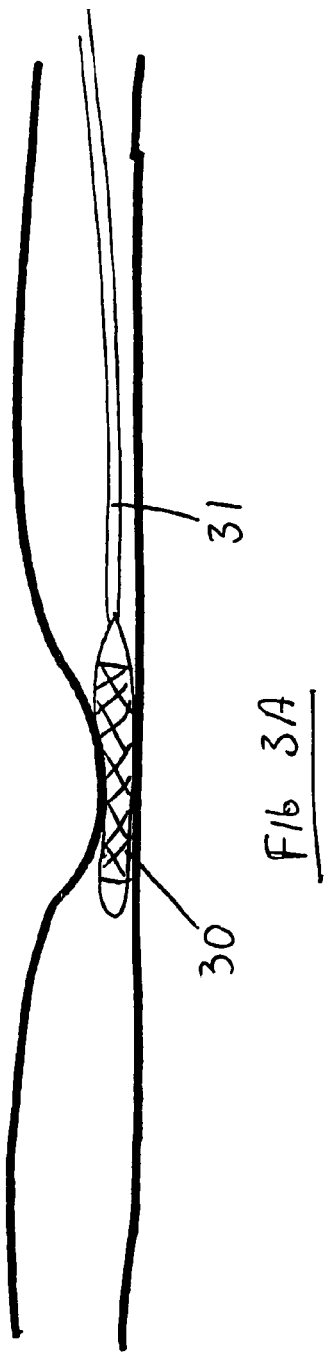
FIG. 3 is a diagram showing the advancement and deployment of the BRIDGE, utilizing a catheter with an expandable element, within a compressed bone segment

While the invention will be described in connection with the preferred embodiment, it will be understood that it is not intended to limit the invention to that embodiment

DETAILED DESCRIPTION OF THE PREFERRED EMBODIMENT

Throughout the description the term BRIDGE refers to a expandable device that is used to fixate or repair bone fractures. The device may be made of metals such as stainless steel, tantalum, titanium, Nitinol or Elgiloy and it may form an electrode for electrical stimulation. One or more electrodes may be associated with it. The BRIDGE may incorporate fiber optics for imaging, sensing, or the transmission of energy to heat, ablate, or illuminate. The device may also be made from a plastic or other non-metallic material. The BRIDGE may also incorporate a covering of polymer or other materials. The BRIDGE may also be a composition of different materials. The BRIDGE may be smooth or have cutting or abrasive surfaces. The BRIDGE can be self-expanding or use a device such as a balloon catheter to mechanically expand or further expand it. In addition, other means of expanding the BRIDGE may be utilized such as any mechanical means of expansion, or thermal, vibrational, electrical, hydraulic, pneumatic actuation. Mechanical means might employ a system consisting of a rubber grommet that expands when it is compressed axially. Another mechanical means of expansion may use a tubular array of elements such as splines, wires or braided wire that expand radially outward when compressed at each end. Another mechanical means could employ wedges in a tubular or cylindrical type of array that collectively force the BRIDGE to expand when they are moved relative to each other. The BRIDGE delivery system may also employ fiber optic technology in order to endoscopically diagnose, control placement and review procedural outcome. Likewise, a number of other technologies such as pressure monitoring, stress monitoring, volume monitoring, etc. can be employed to benefit the outcome of the procedure.

The BRIDGE may be implanted for chronic use or for acute use. In acute use, the BRIDGE is used for temporary stabilization and fixation of bone fractures. After a period of time, the BRIDGE is withdrawn.

Biodegradable materials that degrade or dissolve over time may be used to form the BRIDGE. Various coatings may be applied to the BRIDGE including, but not limited to, thrombo-resistant materials, electrically conductive, non-conductive, thermo-luminescent, heparin, radioactive, or biocompatible coatings. Materials such as calcium, minerals, or irritants can be applied to the BRIDGE in order to expedite bone growth. Drugs, chemicals, and biologics such as morphine, dopamine, aspirin, genetic materials, antibiotics and growth factors can be applied to the BRIDGE in order to facilitate treatment.

Other types of additives can be applied as required for specific treatments.

Electrically conductive BRIDGEs with electrode elements may be used with companion pulse generators to deliver stimulation energy to the bone to expedite bone growth. This electrical therapy may be used alone or in combination with other therapies to treat the affected site. Electrical therapies may be supplied from implantable devices or they may be coupled directly to external generators. Coupling between the BRIDGE and external generators can be achieved using technologies such as inductive or microwave coupling as examples. The BRIDGE may also be designed of geometries or materials that absorb radioactive energies for the treatment of bone cancer, as an example.

In the preferred embodiment, access is gained to a location on the bone that the device will pass through. A surgical incision is made through tissue to expose the entry site at the bone. The size and scope of the incision is dependent on the need for each case, Preferably, a small hole is drilled through the bone into the medullary cavity (marrow conduit). Larger holes or removal of a portion of the bone may be required dependent on the need for each case.

In the example of a fractured femur, an access location might be the either the greater trochanter or the patellar surface. In the case of a fractured humerus, the access might be made at the greater tubercle or the capitulum.

The device, on its delivery system, is then passed through the marrow cavity and positioned across the fracture.

When the right position is attained (potentially guided by CAT scan, MRI, x-ray, or fluoroscopic imaging), the fracture can be manipulated to an optimum configuration if needed, and the device is expanded or released for expansion. The delivery system is then removed after expansion.

If necessary, the access hole in the bone can be plugged with retained bone chips from the drilling procedure, fibrin or other acceptable materials.

Any surgical incision is closed with standard techniques.

It may be necessary to remove some bone marrow to facilitate placement of the BRIDGE. After placement of the BRIDGE, the marrow can be reinserted into the bone and within the BRIDGE. Another alternative treatment may be to replace the marrow with a polymeric substance that hardens after placement within the bridge and bone portions. This would enhance the immediate fixation strength. The polymeric substance can be biodegradable or otherwise metabolized by the body. In addition, the polymeric substance may incorporate drugs, antibiotics other clinically relevant substances and materials. The polymeric substance can also form a foam or cellular structure to allow for marrow formation.

Other embodiments of the BRIDGE invention can include the use of external screws that join the BRIDGE through the bone. This provides and extra measure of securement and strength.

FIG. 1A is a diagram showing the BRIDGE 10, which is mounted to a balloon catheter delivery device 11 within a segment of fractured bone 12. The entire system is advanced through an opening 13 in the bone 12. The BRIDGE 10 is positioned to span the fracture. At this point, the balloon is inflated causing the BRIDGE to expand against the inside of the bone. The balloon may be inflated via a syringe or pump 14 and a pressure gauge 15. The balloon may have a predetermined minimum or maximum diameter. In addition, the balloon can have a complex shape to provide proper placement and conformance of the device based on anatomical requirements and location. One or more inflations may be used to insure proper positioning and results. FIG. 1B shows the expanded BRIDGE 10 spanning the fracture and connecting the bone segments. The delivery device 11 is being withdrawn. If required, the balloon may be reinserted and reinflated for additional BRIDGE manipulation.

FIG. 2A is a diagram showing a self-expanding BRIDGE 20, which is compressed and inserted within a catheter delivery device 21, within a segment of fractured bone 22. The entire system is advanced through an opening 23 in the bone 22. The BRIDGE 20 is positioned to span the fracture.

At this point, the BRIDGE 20 is released from the catheter and self-expands against the inside of the bone. The release mechanism can be simply pushing the BRIDGE out of a catheter lumen or retracting a retaining sleeve. The BRIDGE self-expands due to the spring forces inherent in its materials and design. Likewise, the BRIDGE can be made of a shape-memory material such as Nitinol so that when subjected to body temperature the structure expands. With shape memory materials, the shape of the expanded device can be predetermined. Additionally, the device can be retrieved, repositioned, or removed by using temperature-based shape-memory characteristics.

FIG. 2B shows the expanded BRIDGE 20 spanning the fracture and connecting the bone segments. The delivery catheter 21 is being withdrawn.

In the self-expanding case, the tubular mesh has a predetermined maximum expandable diameter.

FIG. 3A shows a BRIDGE 30 on a balloon catheter 31 being advanced into a crushed area of a bone.

Figure 3B:
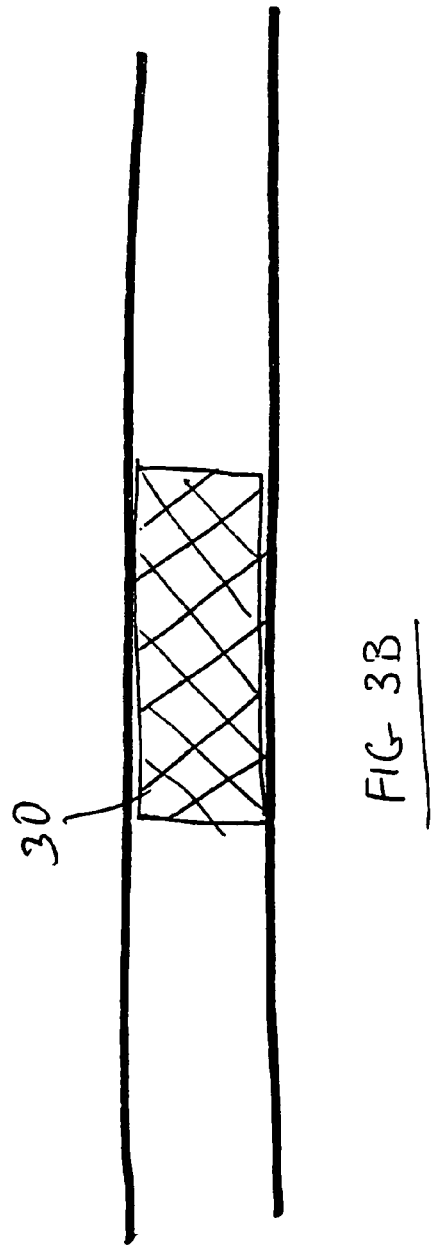

FIG. 3B shows the BRIDGE 30 expanded within the crush zone causing the crushed bone to resume its original diameter. The same results can be attained using any of the aforementioned BRIDGE designs, such as self-expanding or manually expanded, and placement methods. In the case of self-expanding designs, further expansion of the BRIDGE can be performed using a balloon catheter or another type of expansion device such as those mentioned within this invention or can use solid dilator rods.

Figure 4:
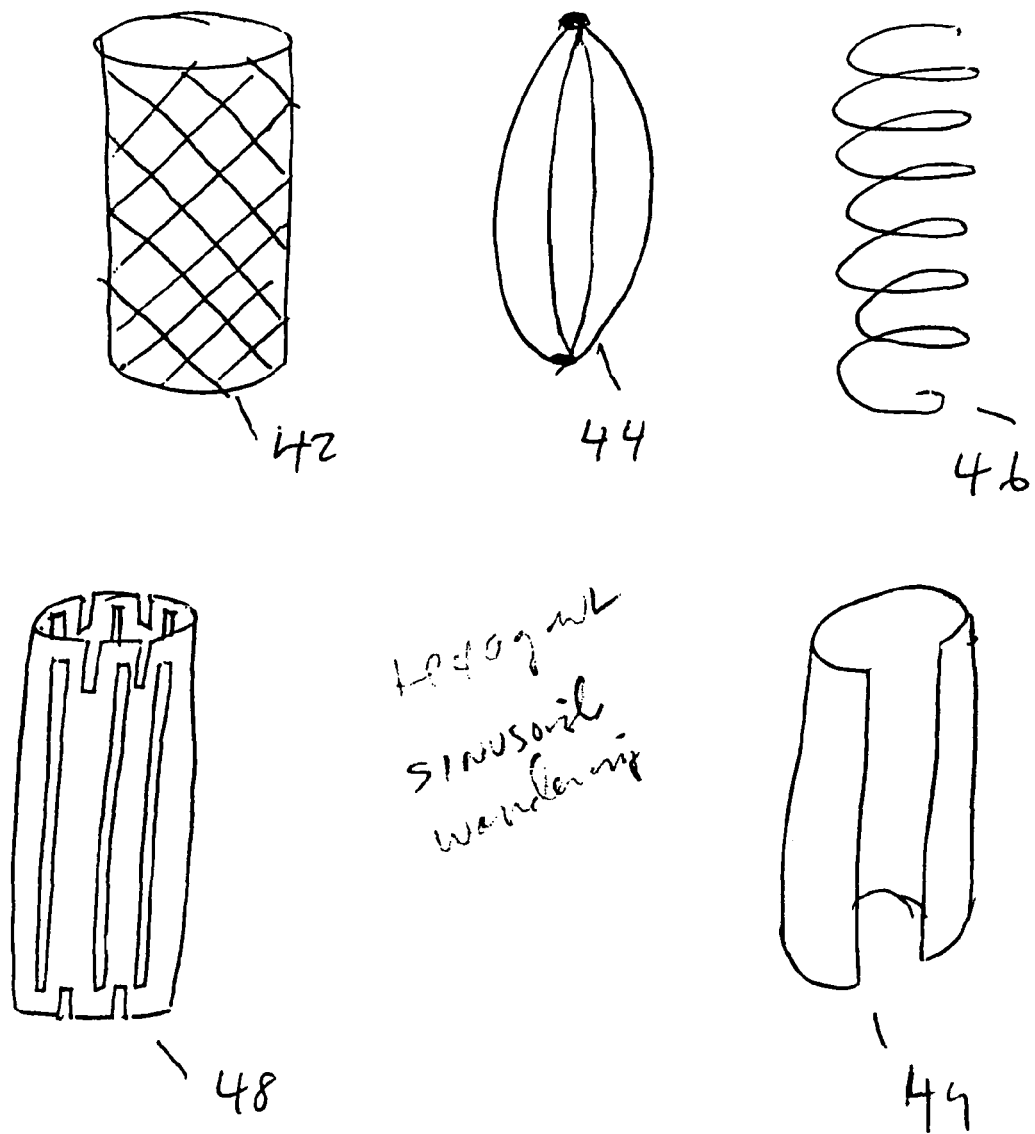
FIG. 4 shows a variety of acceptable BRIDGE structures and designs FIGS. 5A & B depict a bridge that can be expanded or contracted by relative movement of the ends of the structure

FIG. 4 shows a variety of possible BRIDGE shapes and geometries. A tubular mesh 42, a multi-element spline 44, a coil 46, slotted tube 48, and a clam-shell or sleeve 49. In the case of slotted tube, other geometric configurations of the slots (i.e.; hexagonal, sinusoidal, circular, meandering, spiraling, and multigeometric patterns) may be utilized alone or in conjunction with a combination thereof. Likewise, variations in the geometry of any of the BRIDGEs may be altered to achieve desired performance criteria such as radial strength, longitudinal flexibility or stiffness, expansion ease, profile, surface area, mass and volume, and material selection. The elements of the BRIDGE may be porous, have through holes, or have a covering. In addition, the surface of the bridge may be textured, rough, and sharp or have cleats or small pins integrated or attached. Each of the various shapes and geometries may find its own specialized use in the treatment of specific type of bone fractures.

FIG. 5 shows two states of a manually expandable BRIDGE device 51. The device consists of a coaxial shaft 52 and tube 53 arrangement. Attached to the distal end of the shaft 52 and the tube 53 is a braided mesh tube BRIDGE 51. When the shaft 52 and tube 53 are moved opposite of the other by manipulating the proximal ends, the BRIDGE 51 expands 54 or contracts 55. In this case, the BRIDGE 51 can be made of any structure that expands and contracts such as a coil, splined-elements, etc. The various methods of expanding and contracting these structures are, but not limited to, push-pull, rotation, and balloon manipulation. In this type of device, direct connection to either an electrical generator, laser, or monitoring system can be made. In addition, it be envisioned that a device of similar nature be connected to a mechanical energy source, such as rotational or vibrational sources.

FIG. 6 shows a manually expanded BRIDGE 60 with an internal rod 61 and compression nut mechanism 62. One end of the BRIDGE is fixed to one end of the rod 63, while the other end 64 is allowed to move relative to the rod. As the compression nut is tightened, it forces the end 64 of the BRIDGE to move, thus compressing the BRIDGE and forcing it to expand. Using a customized tool, the compression nut is tightened and the BRIDGE expanded until the desired affect is achieved. The nut can have a locking mechanism, such as a lock washer or other means, to maintain position. Alternatively, the nut and rod components can be exchanged for a bolt and nut or a bolt and internally threaded tubular rod. In any event, the expansion is caused by the relative movement of a screw threaded mechanism.

FIG. 7 shows another manually expanded BRIDGE 70 with an internal rod 71 and compression element 72. One end of the BRIDGE is fixed to one end of the rod 73, while the other end 74 is allowed to move relative to the rod. As the compression element is pushed forward, it forces the end 74 of the BRIDGE to move, thus compressing the BRIDGE and forcing it to expand. The compression element is advanced and the BRIDGE expanded until the desired affect is achieved. The element can maintain its position utilizing mechanical friction or a detent mechanism. Other means of maintaining position are possible. The internal rod of the manually expanded BRIDGEs may be flexile or rigid. The expanding elements of the manually expanded BRIDGEs may utilize geometries such as those discussed in FIG. 4

FIGS. 8A & 8B show the use of a coil BRIDGE. The coil BRIDGE 81 is advanced to the fracture in a stretched state with a diameter less than its natural, unstretched diameter. When it is released from the delivery device 82, the coil BRIDGE expands to a state of greater diameter. As it expands to a greater diameter 83 it naturally shortens in length. This simultaneously draws the fracture together and fixates the fracture.

FIGS. 9A & 9B show the use of a braid BRIDGE. The braid BRIDGE 91 is advanced to the fracture in a stretched state with a diameter less than its natural, unstretched diameter. When it is released from the delivery device 92, the braid BRIDGE 93 expands to a state of greater diameter. As it expands to a greater diameter it naturally shortens in length. This simultaneously draws the fracture together and fixates the fracture. The devices in FIG. 8 and FIG. 9 can utilize other geometries that function similarly with similar results. In addition, shape memory materials that exhibit similar change of length and diameter may be used in the construction of devices in FIG. 8 and FIG. 9.

FIG. 10 shows the BRIDGE 100 invention including the use of external screws 101 that join the BRIDGE through the bone. This provides an extra measure of securement and strength.

Figure 11:
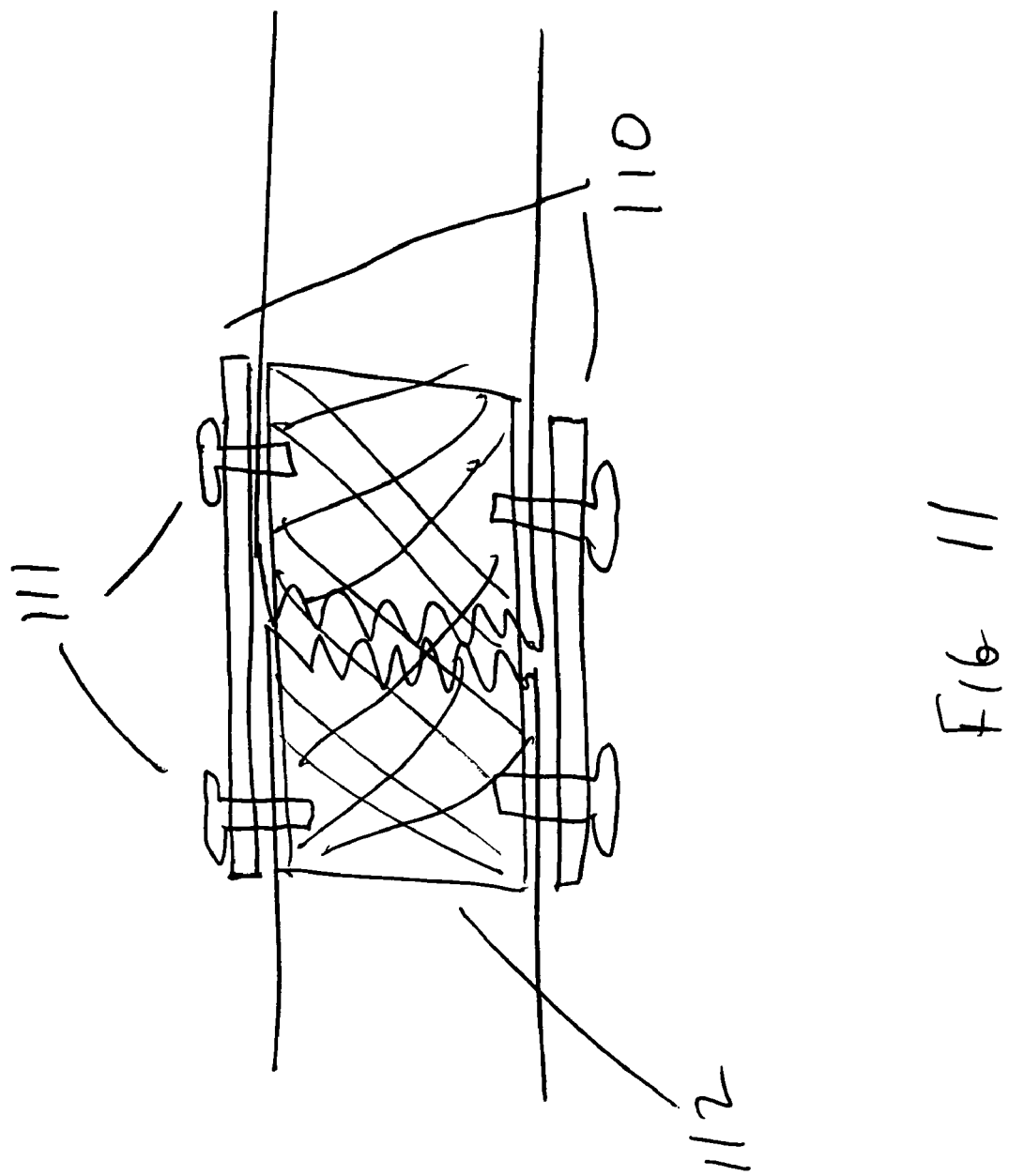
FIG. 11 shows a BRIDGE used in conjunction with external supporting elements

FIG. 11 shows external plates 10 incorporated with this combination of external screws 111 and BRIDGE 112. There may be fractures that require the additional stabilization that this combination provides.

Figure 12:
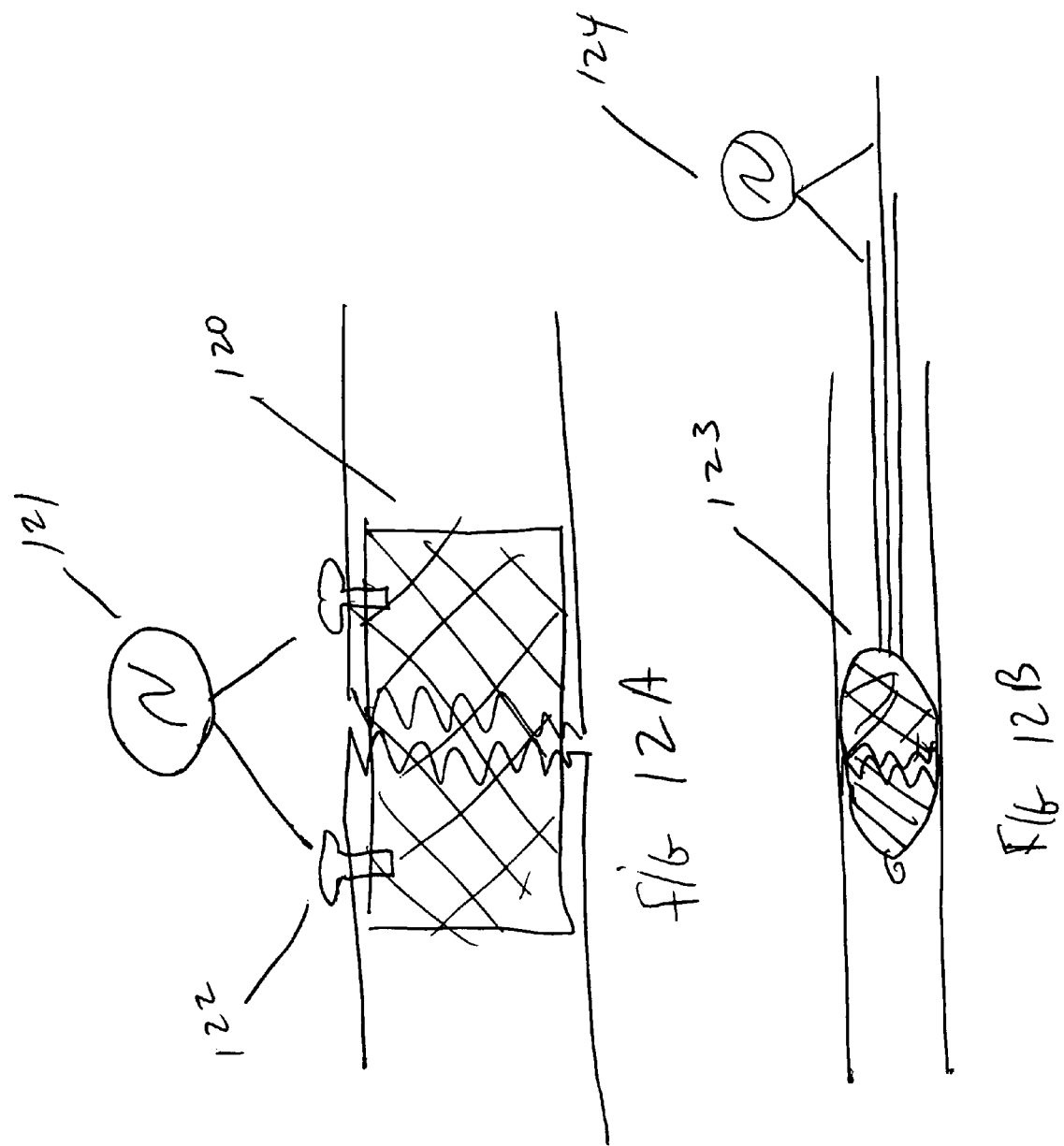
FIGS. 12A & 12B shows an implanted BRIDGE connected to an electrical generator.

FIG. 12A shows an implanted bridge 120 connected to an electrical generator 121 in order to expedite bone growth. The external screws in FIG. 10 can serve the dual purpose of adding securement and acting as electrodes 122.

FIG. 12B shows a device 123 similar to that in FIG. 5 that is connected to an electrical generator 124. In this scenario, the BRIDGE can be used is in a temporary or permanent fashion. It may be desirable to remove the BRIDGE after the bone has healed.

Figure 13:
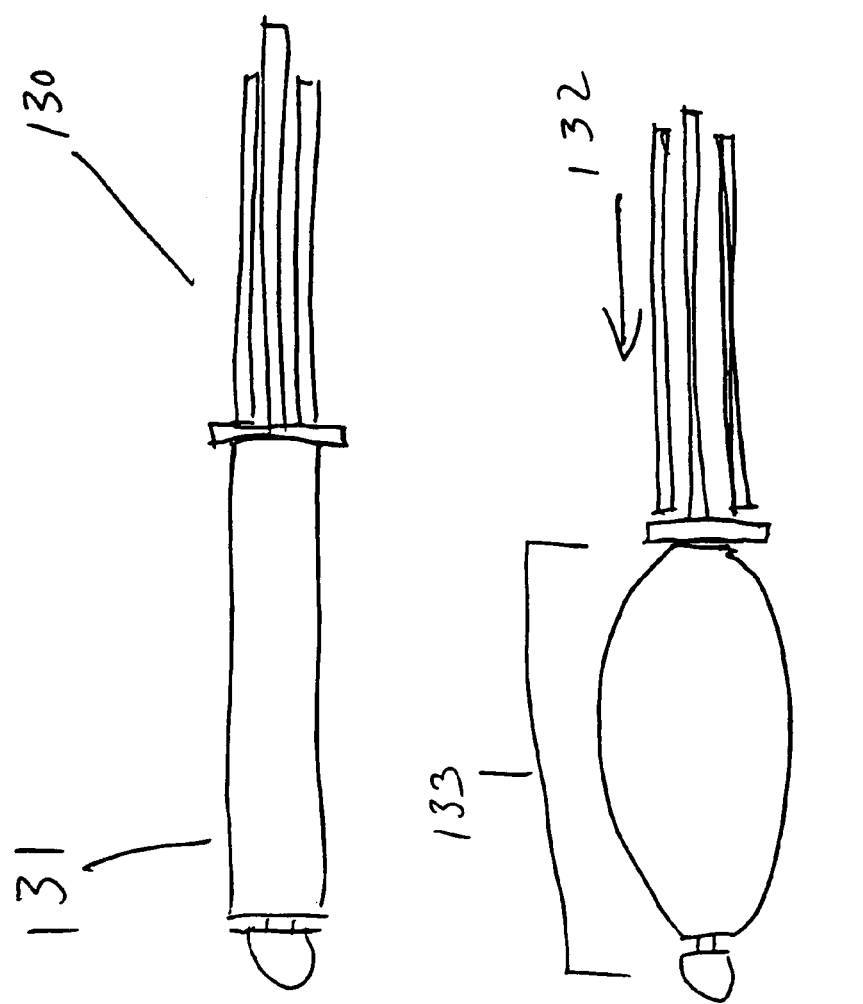
FIG. 13 shows an expansion device using a rubber grommet

FIG. 13 shows a expansion device 130 that uses a rubber sleeve or grommet 131 that when compressed axially 132, expands radially 133.

It should be apparent that various modifications might be made to the devices and methods by one of ordinary skill in the art, without departing from the scope or spirit of the invention.

What is claimed is:

1. A system for treating bone fractures comprising;
    an expandable tubular implant configured to expand from a reduced configuration to an expanded configuration, the expanded configuration comprising a greater diameter and a shorter axial length than the reduced configuration
    a delivery device comprising a balloon, the balloon having an exterior surface,
    said expandable tubular implant removably attached to the exterior surface of the balloon, whereby the balloon expands the tubular implant at the treatment site from the reduced configuration to the expanded configuration, whereby the balloon is configured to be removed after leaving the expanded tubular implant in place to span and fixate the bone fracture, and the expanded tubular implant includes a hardenable substance.

2. The system as in claim 1 wherein said expandable tubular implant comprises a tubular mesh.

3. The device as in claim 1 wherein said device has multiple splines.

4. The device as in claim 1 wherein said device is a coil.

5. The device as in claim 1 wherein said device is a slotted tube.

6. The device as in claim 1 wherein electrical energy is delivered.

7. The device as in claim 1 wherein the device has a coating.

* * * * *

UNITED STATES PATENT AND TRADEMARK OFFICE
CERTIFICATE OF CORRECTION

| | | |
|---|---|---|
| PATENT NO. | : 8,007,498 B2 | Page 1 of 1 |
| APPLICATION NO. | : 09/733775 | |
| DATED | : August 30, 2011 | |
| INVENTOR(S) | : Hans A. Mische | |

It is certified that error appears in the above-identified patent and that said Letters Patent is hereby corrected as shown below:

Col. 6, Line 44
   Insert --;-- after configuration

Col. 6, Line 46
   Delete ","
   Insert --;--

Signed and Sealed this
Twenty-seventh Day of November, 2012

David J. Kappos
*Director of the United States Patent and Trademark Office*